United States Patent

Jones et al.

[11] Patent Number: 5,380,714
[45] Date of Patent: Jan. 10, 1995

[54] 2-FURYL-TRIAZALO [1,5-A]-[1,3,5]TRIAZINES AND PYRAZOLO [2,3-A][1,3,5]TRIAZINES

[75] Inventors: Geraint Jones, Macclesfield; Roger James, Congleton; Rodney B. Hargreaves, Poynton, all of England

[73] Assignee: Imperial Chemical Industries PLC, London, England

[21] Appl. No.: 979,549

[22] Filed: Nov. 20, 1992

[30] Foreign Application Priority Data

Nov. 25, 1991 [GB] United Kingdom ............... 9125002

[51] Int. Cl.$^6$ .................... A61K 31/70; C07H 17/00; C07D 487/04
[52] U.S. Cl. ........................ 514/25; 536/4.1; 514/246; 544/198; 544/207; 544/212
[58] Field of Search ............... 544/198, 207, 212, 209; 514/245, 25; 536/4.1

[56] References Cited

U.S. PATENT DOCUMENTS

| | | | |
|---|---|---|---|
| 3,846,423 | 11/1974 | Kobe et al. | 260/248 |
| 3,995,039 | 11/1976 | Rooney et al. | 424/249 |
| 4,133,674 | 1/1979 | Cartwright et al. | 544/212 |

(List continued on next page.)

FOREIGN PATENT DOCUMENTS 0172608  2/1986 European Pat. Off. .

(List continued on next page.)

OTHER PUBLICATIONS

Ried et al. Tetrahedron., vol. 44, No. 23, pp. 7155-7162; 1988.

(List continued on next page.)

Primary Examiner—Nicholas Rizzo
Assistant Examiner—P. K. Sripada
Attorney, Agent, or Firm—Cushman Darby & Cushman

[57] ABSTRACT

Compounds of the formula I:

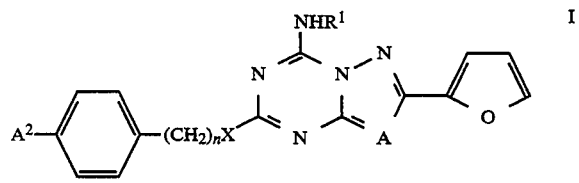

wherein:

X is O, S or NH;

n is O or an integer of from 1 to 3;

$R^1$ is hydrogen, (1–6C)alkyl, or (1–4C)alkanoyl;

$R^2$ is $CH_2R^3$, $NHR^4$, $SO_2NR^5YNR^6R^7$ or $R^8$, in which $R^3$ is hydroxy, (1–4C)alkoxy or (1–4C)alkylsulphonyl; $R^4$ is (1–4C)alkylsulphonyl, (1–4C)haloalkylsulphonyl, formyl, carbamoyl or 2,6-dichloro-4-(2-(1,1-dimethylethyl)amino-1-hydroxyethyl)phenyl; $R^5$ is hydrogen or (1–4C)alkyl; Y is CO or (1–6C)alkylene; $R^6$ and $R^7$ are independently (1–4C)alkyl, or $R^6$ is hydrogen and $R^7$ is (1–4C)alkyl, (1–4C)haloalkyl, phenyl(1–4C)alkyl or, when Y is (1–6C)alkylene, is (1–4C)alkylaminocarbonyl or (5–6C)cycloalkylaminocarbonyl; and $R^8$ is a sugar residue of formula II in which $R^9$ represents hydrogen, methyl or hydroxymethyl and m is 2 or 3;

A is N or CT in which T is hydrogen or (1–4C)alkyl; or a pharmaceutically acceptable salt thereof, processes for their manufacture and pharmaceutical compounds containing them. The compounds are useful as adenosine antagonists.

10 Claims, No Drawings

U.S. PATENT DOCUMENTS

| | | | |
|---|---|---|---|
| 4,560,689 | 12/1985 | Yokoyama | 514/250 |
| 4,565,815 | 1/1986 | Kim et al. | 544/207 |
| 4,713,383 | 12/1987 | Francis et al. | 544/251 |
| 4,734,413 | 3/1988 | Wade | 544/212 |
| 4,996,195 | 2/1991 | Ronsen et al. | 514/25 |
| 5,006,156 | 4/1991 | Gesing et al. | 544/207 |
| 5,164,375 | 11/1992 | Von Middlesworth et al. | 514/25 |
| 5,280,111 | 1/1994 | Shoji et al. | 536/4.1 |

FOREIGN PATENT DOCUMENTS

| | | |
|---|---|---|
| 207651 | 1/1987 | European Pat. Off. . |
| 217748 | 4/1987 | European Pat. Off. . |
| 263071 | 4/1988 | European Pat. Off. . |
| 383589 | 8/1990 | European Pat. Off. . |
| 459702 | 12/1991 | European Pat. Off. . |
| 743316 | 7/1974 | South Africa . |
| 2016002 | 9/1979 | United Kingdom . |
| 2134107 | 8/1984 | United Kingdom . |

OTHER PUBLICATIONS

Strohmeyer, et al., Journal of Heterocyclic Chemistry, "New Synthesis of 2,4-dialkyl(or diaryl) . . . ", vol. 22, 7, Jan. 1985, pp. 7–10.

Journal of Medicinal Chemistry, 16 (4), 312–319, (1973).

Gribel, et al., NeuroReport, 2, 139–140, "Behavioural Effects of Selective $A_2$ Adenosine Receptor . . . ". 1991.

Langdon, et al., J. Chem. Soc., Perkins Trans I, 993–998, "Triazines and Related Products . . . ", 1984.

Callis, et al., J. Pharmacology and Experimental Therap., 1989, 248(3), 1123–1129, "Ihibition of Renal Vasoconstriction . . . ".

Senga, et al., J. Med. Chem., 1982, 25, 243–249, "Synthesis and Enzymic Activity of Various Substituted . . . ".

Miller, et al., Advances in Cyclic Nucleotide and Protein Phosphorylation Research, 16, 277–290, 1984, "Inhibition of Cyclic AMP . . . ".

Reid, et al., Tetrahedron, 44, 23, 7155–7162, 1988, "Synthesis of New Substituted Pyrazolo . . . ".

2-FURYL-TRIAZALO [1,5-A]-[1,3,5]TRIAZINES AND PYRAZOLO [2,3-A][1,3,5]TRIAZINES

This invention concerns novel azole derivatives and, more particularly, certain 2-heteroaryl-triazolo[1,5-a][1,3,5]triazines and pyrazolo[2,3-a][1,3,5-]triazines which have useful pharmacological properties (and in particular antagonise the actions of adenosine such as vasodilation). The invention also includes pharmaceutical compositions containing the novel azole derivatives for use in treating certain diseases and disorders affecting mammalian cardiac, peripheral and/or cerebral vascular systems. Also included are processes for the manufacture and formulation of the novel azole derivatives.

The compound theophylline (1,3-dimethylxanthine) has been used clinically (usually as its ethylene diamine salt, which is also known as aminophylline) as a respiratory stimulant, a centrally acting stimulant, a bronchodilator, a cardiac stimulant and as a diuretic. This diversity of clinical uses is an indication of the range of pharmacological actions which have been attributed to theophylline. These include phosphodiesterase inhibition, adenosine receptor antagonism, mobilisation of intracellular calcium and the release of catecholamines. Recently theophylline has also been reported to be useful in treating myocardial ischaemia (Maseri et al., *The Lancet*, 1989, 683–686), skeletal muscle ischaemia (Picano et. al., *Angiology*, 1989, in press) and cerebral ischaemia (Skinhoj et al., *Acta. Neurol. Scand.*, 1970, 46, 129–140). The beneficial effects of theophylline in these ischaemic disorders are believed to be due to a reduction or prevention of the phenomenon known as "vascular steal" by virtue of the compound's ability to antagonise the actions of adenosine by blocking the adenosine receptors which mediate metabolism-linked vasodilatation.

The "vascular steal" phenomenon can occur when the major artery supplying a particular vascular bed is partially or totally occluded resulting in ischaemia. In this situation, the compromised vascular bed dilates and blood flow is maintained by either an increase in flow across the narrowed vessel or by an increase in flow through the collateral vessels. However, increased metabolic activity in adjacent vascular beds results in release of mediators such as adenosine, causing them to dilate, resulting in the limited blood flow to the compromised vascular bed being "stolen" by these adjacent areas. The loss of blood from compromised to normally perfused vascular beds by the phenomenon of "vascular steal" further diminishes the blood flow in the compromised vascular bed.

The diversity of pharmacological properties possessed by theophylline make it difficult to use in the regular treatment or prevention of occlusive diseases and conditions of the vasculature. Thus, its associated action as a phosphodiesterase inhibitor results in cardiac stimulation which is deleterious for patients with myocardial ischaemia. Furthermore, the relatively low potency of theophylline means that dose-levels which are therapeutically useful are close to those which can cause serious central side-effects.

Certain 2-heteroaryl-pyrazolo[2,3-a][1,3,5]triazines are known from W. Ried and S. Aboul-Fetouh, Tetrahedron, 44(23), 7155–7162, 1988. In addition, European patent application publication no. EP A2 383589 names certain other 2-heteroaryl-pyrazolo[2,3-a][1,3,5]triazines, although no details of their preparation are given. No therapeutic use is ascribed to any of these compounds.

Several triazolo[1,5-a][1,3,5]triazines and pyrazolo[2,3-a][1,3,5]triazines, which do not have a 2-heteroaryl substituent, have been ascribed therapeutic uses. Thus, certain triazolo[1,5-a][1,3,5]-triazines have been disclosed as bronchodilators (see U.S. Pat. No. 4,734,413). Certain pyrazolo[2,3-a][1,3,5]triazines have been variously disclosed as inhibitors of gastric acid secretion (see British patent application publication no. 2134107 and European patent application publication no. EP A2 0172608); as antiinflammatory agents (see European patent applications publication nos. EP A2 0172608 and EP A2 207651); as bronchodilators (see British patent application publication no. GB 2016002, Belgian patent no. 815405 and U.S. Pat. No. 3995039), and as phosphodiesterase inhibitors (see U.S. Pat. No. 3846423).

We have now discovered (and this is a basis for our invention) that a group of novel 2-heteroaryl-triazolo[1,5-a][1,3,5-triazines and pyrazolo[2,3-a][1,3,5]triazines of formula I defined below are effective antagonists of the actions of adenosine and in particular of its vasedilatory actions.

According to the invention there is provided a compound of the formula I set out hereinafter (together with the other formulae appearing in Roman numerals) wherein:

X is O, S or NH;
n is O or an integer of from 1 to 3;
$R^1$ is hydrogen, (1–6C)alkyl, or (1–4C)alkanoyl;
$R^2$ is $CH_2R^3$, $NHR^4$, $SO_2NR^5YNR^6R^7$ $R^8$, in which $R^3$ is hydroxy, (1–4C)alkoxy or (1–4C)alkylsulphonyl; $R^4$ is (1–4C)alkylsulphonyl, (1–4C)haloalkylsulphonyl, formyl, carbamoyl or 2,6-dichloro-4-(2-(1,1-dimethylethyl)amino-1-hydroxyethyl)phenyl; is hydrogen or (1–4C)alkyl; Y is CO or (1–6C)alkylene; $R^6$ and $R^7$ are independently (1–4C)alkyl, or $R^6$ is hydrogen and $R^7$ is (1–4C)alkyl, (1–4C)haloalkyl, phenyl(1–4C)alkyl or, when Y is (1–6C)alkylene, is (1–4C)alkylaminocarbonyl or (5–6C)cycloalkylaminocarbonyl; and $R^8$ is a sugar residue of formula II in which $R^9$ represents hydrogen, methyl or hydroxymethyl and m is 2 or 3;
A is N or CT in which T is hydrogen or (1–4C)alkyl;
or a pharmaceutically acceptable salt thereof.

It will be appreciated that depending on the nature of the substituents, in containing one or more chiral centres, the formula I compounds may exist in and be isolated in one or more different enantiomeric or racemic forms (or a mixture thereof). It is to be understood that the invention includes any of such forms which possesses the property of antagonising the actions of adenosine, it being well known how to prepare individual enantiomeric forms, for example, by synthesis from appropriate chiral starting materials or by resolution of a racemic form. Similarly, the adenosine antagonist properties of a particular form may be readily evaluated, for example by use of one or more of the standard in vitro or in vivo screening tests detailed hereinbelow.

A particular value for $R^1$ when it is alkyl is, for example, methyl, ethyl, propyl or butyl, and when it is alkanoyl is, for example, formyl, acetyl or propionyl. $R^1$ is preferably hydrogen.

A particular value for T when it is alkyl is, for example, methyl, ethyl or propyl. T is preferably hydrogen.

N is a preferred value for A.

A particular value for $R^3$ when it is (1–4C)alkoxy is, for example methoxy or ethoxy.

A particular value for $R^3$ when it is (1–4C)alkylsulphonyl is, for example, methylsulphonyl or ethylsulphonyl.

A particular value for $R^4$ when it is (1–4C)alkylsulphonyl is, for example, methylsulphonyl, ethylsulphonyl or butylsulphonyl, and when it is (1–4C)haloalkylsulphonyl is, for example, trifluoromethylsulphonyl.

A particular value for $R^5$ when it is (1–4C)alkyl is, for example methyl or ethyl.

A particular value for Y is, for example, ethylene, propylene or butylene.

Particular examples of values for $R^6$ and $R^7$ are; for (1–4C)alkyl, methyl or ethyl; for (1–4C)haloalkyl, trifluoromethyl; for phenyl(1–4C)alkyl, benzyl; for (1–4C)alkylaminocarbonyl, methylaminocarbonyl; and for (5–6C)cycloalkylaminocarbonyl, cyclopentylaminocarbonyl. For example, $R^6$ and $R^7$ may both represent methyl groups.

The integer n may be 1, 2 or 3. Preferably it is 2.

Particular values for $R^8$ include, for example, those wherein m is 3 and:

$R^9$ is hydrogen, e.g., L-arabinofuranosyl or D-xylofuranosyl;

$R^9$ is methyl, e.g., 6-deoxy-D-galactopyranosyl or 6-deoxy-L-galactopyranosyl; and $R^9$ is hydroxymethyl, e.g., D-galactopyranosyl, D-glucopyranosyl, or D-mannopyranosyl.

A preferred value for X is NH.

Particular pharmaceutically acceptable salts include, for example, salts with acids affording physiologically acceptable anions, for example, salts with strong acids, such as hydrochloric, hydrobromic, sulphuric, phosphoric, methanesulphonic and trifluoracetic acids. In addition, for those compounds of formula I which are sufficiently basic, suitable salts include, for example, salts with organic acids affording a physiologically acceptable anion such as salts with oxalic, citric or maleic acid. Certain compounds of formula I, for example those in which $R^2$ comprises a sulphonamide group, may form base salts with bases affording physiologically acceptable cations, such as alkali metal and alkaline earth metal salts.

Specific compounds of the formula I which are of interest are described hereinafter in the accompanying Examples, and pharmaceutically acceptable salts thereof, and these are provided as a further feature of the invention.

The compounds of formula I may be manufactured using procedures analogous to those well known in the arts of heterocyclic and organic chemistry for the production of structurally analogous compounds. Such procedures are included as a further feature of the invention and include the following preferred procedures for the manufacture of a compound of the formula I in which $R^1$, $R^2$, n, X, and A have any of the meanings defined above:

(a) The reaction of a compound of the formula III in which Z is a suitable leaving group, for example hydrocarbylsulphonyl such as (1–6C)alkylsulphonyl (such as methylsulphonyl or ethylsulphonyl), aryloxy (such as phenoxy), or halogeno (such as chloro or bromo), with a compound of the formula IV.

The process is generally carried out under basic conditions. These may be conveniently provided by the inherent basicity of the compound of formula IV itself, for example when X is imino. Alternatively, the basic conditions may be provided by adding a suitable base to the reaction mixture. Suitable bases include, for example, tertiary amines such as trimethylamine, triethylamine, pyridine, 2,6-dimethylpyridine and 1,8-diazabicyclo[5.4.0]undec-7-ene. It will be appreciated that the basic conditions may also be provided by using the compound of the formula IV in the form of a salt such as an alkali metal salt, for example, a lithium, sodium or potassium salt. Such a salt may be prepared separately, or formed in situ immediately prior to performing the above process (a), by any conventional method, for example by reacting the compound of the formula IV with an alkali metal (1–4C)alkoxide, hydroxide or hydride in a suitable solvent or diluent such as acetonitrile, 1,2,-dimethoxyethane, t-butyl methyl ether, tetrahydrofuran, ethanol or N,N-dimethylformamide.

The process (a) will generally be performed at a temperature in the range, for example, 10° to 120° C. and conveniently in the range 15° to 80° C. and in a suitable solvent or diluent such as acetonitrile, ethanol, tetrahydrofuran, 1,2-dimethoxyethane, t-butyl methyl ether or N,N-dimethylformamide.

The starting materials of formula III may be obtained by standard procedures well known in the art. Thus, for example, those compounds of formula III in which Z is alkylsulphonyl may be made by oxidation of the corresponding alkylthio derivative of formula V in which $R^{10}$ is (1–6C)alkylthio, using a conventional oxidant such as a peracid, for example, peracetic, perbenzoic or 3-chloroperbenzoic acid, conveniently at a temperature in the range, for example, 0° to 40° C., and in a suitable solvent or diluent such as dichloromethane or chloroform. Similarly, those compounds of the formula III in which Z is chloro or bromo may be obtained, for example, by reacting an alkylthio derivative of formula V (especially in which $R^{10}$ is methylthio or ethylthio) with chlorine or bromine in the presence of hydrogen chloride or hydrogen bromide, respectively, at a temperature in the general range, for example, −20° to 15° C. and in a generally inert polar solvent such as ethanol or 2-propanol. The compounds of formula III in which Z is phenoxy may conveniently be prepared by a method analagous to process (a), but starting from a phenol instead of a compound of formula IV and a compound of formula III in which Z is a hydrocarbylsulphonyl group.

The starting alkylthio starting materials of formula V may themselves be obtained, for example, by reaction of a compound of the formula VI with the appropriate dialkyl N-cyanodithioiminocarbonate of formula VII, in which $R^{10}$ has any of the meanings defined above, at elevated temperature in the range, for example, 60° to 200° C., conveniently as a melt in the absence of solvent or diluent, to give the compound of formula VI in which $R^1$ is hydrogen. When a compound of formula I in which $R^1$ is alkyl or alkanoyl is required, the compound of formula V in which $R^1$ is hydrogen may be alkylated or acylated in conventional manner.

The starting compounds of formula VI wherein A is N may themselves be obtained, for example by reacting the appropriate iminoether of the formula Q.C(OR)=NH in which Q is 2-furyl and R is (1–4C)alkyl such as methyl or ethyl (formed from the corresponding nitrile of the formula Q.CN and alcohol of the formula R.OH in the presence of an anhydrous acid such as hydrogen chloride) with an aminoguanidine salt (especially the nitrate) in the presence of a suitable base, such as pyridine or 2,6-utidine, which may also be used as the reaction solvent, at a temperature in the range, for example, 60°–120° C.

The starting compounds of formula VI wherein A is CT may themselves be obtained, for example by reacting the appropriate ester of the formula $Q.CO_2R$ (in which Q is 2-furyl and R is lower alkyl such as methyl or ethyl) under basic conditions with an alkali metal salt of the formula T.CHM.CN (in which M is an alkali metal such as sodium or lithium), conveniently produced in situ by adding a nitrile of the formula $T.CH_2.CN$ to a solution of the alkali metal in liquid ammonia, to give the corresponding cyanoalkylketone of the formula Q.CO.CH(T).CN. The latter compound is then cyclised with hydrazine, for example by heating in a suitable solvent or diluent such as ethanol or propanol to give the required pyrazole of formula VI.

The starting compounds of formula IV may be prepared by conventional methods. For example, the compounds of formula IV in which $R^2$ represents $SO_2N$-$R^5YNR^6R^7$ may be prepared by reacting a diamine of formula $HNR^5YNR^6R^7$ with the appropriate 4-substituted benzenesulphonyl halide or a protected derivative thereof, followed if necessary by the removal of the protecting group.

(b) For those compounds of formula I in which $R^2$ is $R^8$, a compound of formula VIII or a salt thereof is reacted with a compound of formula IX in which $Z^1$ is a leaving group, such as a halogen atom (for example a bromine atom).

The process is generally carried out under basic conditions. These may be provided by adding a suitable base to the reaction mixture. Suitable bases include, for example, tertiary amines such as trimethylamine, triethylamine, pyridine, 2,6-dimethylpyridine and 1,8-diazabicyclo[5.4.0]undec-7-ene. It will be appreciated that the basic conditions may also be provided by using the compound of the formula VIII in the form of a salt such as an alkali metal salt, for example, a lithium, sodium or potassium salt. Such a salt may be prepared separately, or formed in situ immediately prior to performing the above process (b), by any conventional method, for example by reacting the compound of the formula VIII with an alkali metal (1–4C)alkoxide, hydroxide or hydride in a suitable solvent or diluent such as acetonitrile, 1,2,-dimethoxyethane, t-butyl methyl ether, tetrahydrofuran, ethanol or N,N-dimethylformamide.

The process (b) will generally be performed at a temperature in the range, for example, 10° to 120° C. and conveniently in the range 15° to 80° C. and in a suitable solvent or diluent such as acetonitrile, ethanol, tetrahydrofuran, 1,2-dimethoxyethane, t-butyl methyl ether or N,N-dimethylformamide.

The compounds of formula VIII may be obtained by reacting a compound of formula III with a compound of formula X according to a method analagous to that of process (a) above.

(c) For those compounds of formula I in which $R^2$ is $R^8$, a corresponding compound of formula I in which one or more of the sugar hydroxyl groups is protected is deprotected.

The protecting group(s) and deprotection conditions are those well known in the art for use with sugar hydroxyl groups and which are compatible with the presence of other reactive groups in the formula I compound. Thus, for example, an acetyl group may be removed by acid catalysed hydrolysis.

The protected derivatives of formula I may be prepared by a method analagous to that of process (a) or (b) above, but starting from an appropriately protected starting material.

(d) For those compounds of formula I in which $R^2$ represents $NHR^4$ and R4 represents (1–4C)alkylsulphonyl or (1–4C)haloalkylsulphonyl, reacting a compound of formula XI with a compound of formula $R^4Z^2$ in which $Z^2$ is a leaving group such as a halogen atom (for example chlorine or bromine).

The reaction may conveniently be performed at a temperature in the range of from 0° to 100° C., preferably from 10° to 80° C. Suitable solvents for the reaction include halogenated hydrocarbons such as dichloromethane and ethers such as tetrahydrofuran.

The starting compounds of formula XI may be prepared by reacting a compound of formula XII or a protected derivative thereof (for example an N-acetyl or N-benzyl derivative) with a compound of formula III according to a method analagous to that of process (a) above. If necessary, the protecting group may then be removed using a conventional technique.

It will be appreciated that those compounds in which $R^1$ is other than hydrogen may also be obtained by carrying out a conventional alkylation or acylation of the corresponding formula I compound in which $R^1$ is hydrogen obtained by one of processes (a) to (d) above.

Whereafter, when a pharmaceutically acceptable salt is required, it may be obtained, for example, by reacting a compound of formula I with the appropriate acid or base affording a physiologically acceptable ion or by another conventional procedure.

Similarly, when an optically active form of a chiral compound of formula I is required, either one of processes (a) to (d) above may be carried out using the appropriate optically active starting material or else a racemic form may be resolved by a conventional procedure, for example, using an optically active form of a suitable acid.

Certain of the starting materials used in the processes according to the invention are novel, and these are provided as further aspects of the invention. For example, the invention provides compounds of formula IV and XI.

As stated above, the compounds of the invention possess the property of antagonising one or more of the physiological actions of adenosine and are valuable in the treatment of diseases and medical conditions affecting the mammalian cardiac, peripheral and/or cerebral vascular systems, such as ischaemic heart disease, peripheral vascular disease (claudication) and cerebral ischaemia. The compounds may also be useful in the treatment of migraine.

The effects of compounds of formula I as adenosine receptor antagonists may be demonstrated in one or more of the following standard in vitro and/or in vivo tests.

(a) $A_2$ Adenosine receptor affinity test

This test involves the ability of a test adenosine antagonist to displace the known adenosine mimetic agent [$^3$H]-N-ethylcarboxamidoadenosine (NECA) from binding sites on membrane preparations derived from the rat phaeochromocytoma cell line PC 12 (available from the Beatson Institute, Glasgow). The basic procedure has been described by Williams et al. (J. Neurochemistry, 1987, 48(2), 498–502).

The membrane preparation is obtained as follows:

Frozen pellets of PC12 cells are washed twice with ice cold, buffered, physiological saline and the cells recovered by centrifugation (1500 G) at 3° C. The separated cells are then suspended in hypotonic solution (distilled water), allowed to stand on ice for 30 minutes and are then carefully homogenized using a standard high-speed homogeniser with periodic ice-cooling to obtain a fine suspension. The homogenate is centrifuged (48000 G) and the pellet is resuspended in 50 mM tris-HCl buffer, pH 7.4 containing adenosine deaminase (5 units/ml, Type VIV from calf intestinal mucosa, available from Sigma Chemical Corporation, under reference no. A1280). The mixture is then incubated at 37° C. After 20 minutes, the reaction is terminated by dilution with ice-cold buffer and transfer onto ice. The material obtained containing the cell membranes is recovered by centrifugation and washed by resuspension in buffer and recentrifugation. The pellet produced is then resuspended in ice-cold buffer using a hand-driven homogenizer. The resultant membrane suspension is frozen and stored under liquid nitrogen until required.

Binding studies are carried out in microtitre plates, the assay mixtures being buffered in 50 mM tris-HCl, pH 7.4 at room temperature. The test compound is dissolved in dimethyl sulphoxide (DMSO) and then diluted with assay buffer to give the test solutions. [The final concentration of DMSO is not allowed to exceed 1% by volume, at which level it does not affect radioligand binding to the membrane receptor.] Incubations are performed at 30° C. for 90 minutes in a total volume of 150 $\mu$l comprising the test solution or buffer (50 $\mu$l), tritiated NECA (50 $\mu$l) and membrane suspension (50 $\mu$l). After incubation, the samples are rapidly filtered over glass-fibre mats and the filter mats are washed to remove non-receptor-bound radioligand. Receptor-bound radioligand entrapped on the filter mats is then determined by liquid scintillation counting. Filtration and washing are carried out using a conventional vacuum filtration cell harvester. The specific binding (defined as the difference between the total binding and the non-specific binding) in the presence of the particular test compound is determined and compared with the control value. Results are conveniently expressed as the negative logarithm of the concentration required to cause a 50% displacement of control specific binding ($pIC_{50}$).

In general, compounds of the formula I showing antagonist activity in this assay typically show a $pIC_{50}$ in the above test (a) of 6 or more. Thus for example, the compound of Example 1 herein showed a 93.7% displacement of control binding at a concentration of $10^{-5}$M and 77.7% displacement at $10^{-7}$M, indicating a $pIC_{50}$ of greater than 7. Using the same test procedure, the known compound 1,3-dimethylxanthine typically shows a $pIC_{50}$ of about 5.

(b) Guinea-pig Atrial Bradycardic Test

This test has also been described by Collis et al. (*British J. Pharmacology*, 1989, 97, 1274–1278) and involves the ability of a test compound to antagonise the bradycardic effect of the adenosine mimetic, 2-chloroadenosine, in a beating guinea-pig atrial preparation, an effect mediated via the adenosine receptor known as $A_1$.

The atrial pair preparation may be obtained as follows:

Atrial pairs are obtained from guinea-pigs (Dunkin Hartley strain, 250–400 g males) and mounted in organ baths containing oxygenated Krebs buffer solution (95% $O_2$; 5% $CO_2$) at 37° C. The spontaneously beating atria are then placed under a resting tension of 1 g and allowed to equilibrate for 50 minutes with continuous overflow. Overflow is then stopped and adenosine deaminase (1 Unit/ml) added to prevent the accumulation of endogenously produced adenosine. After equilibration for 15 minutes, a cumulative dose response curve to the adenosine mimetic, 2-chloroadenosine ($10^{-8}$M to $10^{-4}$M) is administered to produce a maximal slowing of atrial rate. After washout during 30 minutes, adenosine deaminase is readministered to the bath which is allowed to equilibrate for 15 minutes. A $10^{-5}$M solution of the test compound in DMSO is then added to the bath which is left to incubate for 30 minutes. Any effect on the beating rate due to the test compound is noted before the dose response curve to 2-chloroadenosine is repeated. Compounds which are adenosine antagonists attenuate the 2-chloroadenosine response.

Test compounds are assessed by comparing dose response curves to 2-chloroadenosine alone with those obtained in the presence of the compound. Competitive adenosine antagonists produce a parallel shift in the 2-chloroadenosine dose response curve. The dose ratio (DR) is calculated from the ratio of the concentration of 2-chloroadenosine to produce a 50% reduction in atrial rate ($ED_{50}$) in the presence of the test compound divided by the $ED_{50}$ concentration of 2-chloroadenosine in the absence of the test compound for each atrial pair. The pA2, which is an estimate of the concentration of antagonist required to give a dose ratio of 2, may be calculated using a standard computational technique. In this test, the known compound, 1,3-dimethylxanthine, typically shows a pA2 of about 5.

(c) Anaesthetised cat blood pressure Test

This test assesses the ability of a test compound to antagonise the fall in diastolic blood pressure produced by administration of the adenosine mimetic, 2-chloroadenosine.

Male cats (2–3 kg) are anaesthetised with sodium pentobarbitone (45 mg/kg, ip). The following blood vessels are catheterised: right jugular vein (for infusion of the anaesthetic at approximately 7 mg/kg per hour as a 3 mg/ml solution in isotonic saline), the left jugular vein (for administration of test agents) and the right common carotid artery (for monitoring blood pressure and pulse rate). The blood gas status and pH are determined, and are maintained within physiological limits, before administration of 2-chloroadenosine. A control dose response curve (DRC) to 2-chloroadenosine (0.3 to 30 $\mu$g/kg) against the fall in diastolic blood pressure is determined. A solution of the test compound in a mixture of 50% v/v polyethylene glycol (PEG) 400 and 0.1M sodium hydroxide is then administered i.v. and after 15 minutes the DRC to 2-chloroadenosine is determined. This procedure is repeated twice with blood gases and pH being monitored and maintained within physiological limits between each DRC. The concentration of 2-chloroadenosine required to cause a 30 mm Hg fall in diastolic blood pressure is then calculated for each dose of test compound and a Schild plot constructed for those which produce a dose ratio (DR) of >2. From this plot a $K_B$ value is determined. Test compounds which are active in this test will possess a $K_B$ value of 1 mg/kg (or much less).

The above Test (c) may conveniently be modified to allow evaluation of orally administered test compounds by administering the test compound to conscious cats with indwelling arterial and venous catheters and measuring the effect in preventing an adenosine induced decrease in blood pressure. Test compounds which are orally active in this test will show significant adenosine antagonist activity at a dose of 1–3 mg/kg or less.

(d) Anaesthetised dog Test

This test involves the assessment of the effects of a test compound on antagonising the actions of adenosine in lowering heart rate and producing vasodilation (as measured by a fall in hind-limb perfusion pressure).

Beagles (12–18 kg) are anaesthetised with sodium pentobarbitone (50 mg/kg, iv). The following blood vessels are catheterised: right jugular vein (for infusion of the anaesthetic at approximately 112 mg per hour as a 3 mg/ml solution in isotonic saline), right brachial vein (for administration of drugs and test agents), right brachial artery (for measurement of systemic blood pressure and pulse rate) and the left carotid artery (for administration of adenosine into the left ventricle). Both vagi, the right femoral and sciatic nerves are ligated and severed. A bolus injection of 1250 U heparin is administered before perfusing the right hindlimb at constant blood flow with blood from the iliac artery. The right leg is tied just below the ankle. Xamoterol (1 mg/kg) is then administered to the animal to stabilise heart rate at a high level and nitrobenzylthioinosine (NBTI, 0.5 mg/kg) to inhibit the uptake of adenosine. The animal is sensitised to adenosine during the equilibration time following NBTI by carrying out a dose response curve (DRC). During this time any blood gas or pH imbalance is corrected. A control DRC is performed followed by up to three DRC's after cumulative administration of the test compound (as described in (c) above). Each DRC is carried out 15 minutes after administration of test compound and after the measured parameters of heart rate and hindlimb perfusion pressure have returned to a stable state. Similarly, blood gases and pH are maintained within physiological limits throughout the evaluation.

The amount of adenosine required to cause a 50% fall in measured parameter ($ED_{50}$) i.e. heart rate and hindlimb perfusion pressure is calculated for each dose of test compound and a Schild plot constructed. From this plot a $K_B$ value is determined for antagonism of heart rate response and vasodilator response to adenosine. Test compounds which are active in this test will possess a $K_B$ value of 1 mg/kg (or much less) for vasodilator response to adenosine.

(e) Anaesthetised cat exercise hyperaemia test

This test involves assessment of the effect of a test compound to antagonise the vasodilatation response which occurs during twitch contraction of skeletal muscle. The vasodilation is mediated partly by the release of endogenous adenosine from the contracting skeletal muscle.

Cats (2.4–3.6 kg) are anaesthetised with sodium pentobarbitone (50 mg.kg$^{-1}$ ip). The following blood vessels are catheterized: left jugular vein (for infusion of anaesthetic, at approximately 0.12 mg$^{-1}$min$^{-1}$ as a 6 mg.ml$^{-1}$ solution in isotonic saline), right external jugular vein (for administration of drugs and test compounds), right common carotid artery (for measurement of systemic arterial blood pressure and pulse rate) and right brachial artery (for withdrawal of blood).

Blood flow to the left hind limb is measured with an electromagnetic flow probe around the left external iliac artery. The whole of the left hind limb is made to contract at 3 Hz for 20 minutes duration by stimulating the sciatic and femoral nerves. Active tension produced by the extensor digitorum longus and peroneous longus muscles is measured isometrically with a force transducer. Exercise is repeated twice within the same animal, in either the absence or presence of the test compound. Test compounds are assessed for their ability to reduce the vasodilatation during skeletal muscle contraction. Test compounds which are active in this test will show significant inhibition of vasodilation during exercise at a dose of 1 mg/kg (or much less).

The compounds of the invention are generally best administered to warm-blooded animals for therapeutic or prophylactic purposes in the treatment or prevention of cardiovascular diseases and adverse conditions in the form of a pharmaceutical composition comprising said compound of formula I or a pharmaceutically acceptable salt thereof, in admixture or together with a pharmaceutically acceptable diluent or carrier. Such compositions are provided as a further feature of the invention.

In general, it is envisaged that a compound of formula I will be administered orally, intravenously or by some other medically acceptable route (such as by inhalation, insufflation, sub-lingual or transdermal means) so that a dose in the general range, for example, 0.001 mg to 25 (and more particularly in the range, for example, 0.05 to 10 mg/kg) mg/kg body weight is received. However, it will be understood that the precise dose administered will necessarily vary according to the nature and severity of the disease or condition being treated and on the age and sex of the patient.

A composition according to the invention may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose from containing, for example, 5–200 mg of the compound of formula I or an equivalent amount of a pharmaceutically acceptable salt thereof.

The compositions may be obtained by conventional procedures using pharmaceutically acceptable diluents and carriers well known in the art. Tablets and capsules for oral administration may conveniently be formed with an enteric coating (such as one based on cellulose acetate phthalate) to minimise the contact of the active ingredient of formula I with stomach acids.

The compositions of the invention may also contain one or more agents known to be of value in the diseases or conditions of the cardiovasculature intended to be treated. Thus, they may contain, in addition to the compound of formula I, for example: a known platelet aggregation inhibitor, prostanoid constrictor antagonist or synthase inhibitor (thromboxane $A_2$ antagonist or synthase inhibitor), cyclooxygenase inhibitor, hypolipidemic agent, anti-hypertensive agent, inotropic agent, beta-adrenergic blocker, thrombolytic agent or a vasodilator.

In addition to their use in therapeutic medicine, the compounds of formula I are also useful as pharmacological tools in the development and standardisation of test systems for the evaluation of new cardiovascular agents in laboratory animals such as cats, dogs, rabbits, monkeys, rats and mice.

The invention will now be illustrated by the following non-limiting Examples in which, unless otherwise stated:

(i) evaporations were carried out by rotary evaporation in vacuo;

(ii) operations were carried out at ambient temperature, that is in the range 18°–26° C.;

(iii) flash column chromatography or medium pressure liquid chromatography (MPLC) was performed on silica gel [either Fluka Kieselgel 60 (catalogue no. 60738) obtained from Fluka AG, Buchs, Switzerland, or Merck Kieselgel Art. 9385, obtained from E Merck, Darmstadt, Germany];

(iv) yields are given for illustration only and are not necessarily the maximum attainable by diligent process development;

(v) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet; q, quartet; and (vi) all end-products were characterised by microanalysis, NMR and/or mass spectroscopy.

EXAMPLE 1

7-Amino-2-(2-furyl)-5-[2-[(4-dimethylaminoethyl-N,methylsulphonamido)phenyl]ethyl]amino[1,2,4]-triazolo[1,5-a][1,3,5]-triazine (4-Dimethylaminoethyl-N-methylsulphonamido)phenylethylamine hydrochloride (4.2 g) was added to a stirred suspension of 7-amino-2-(2-furyl)-5-methylsulphonyl-[1,2,4]triazolo[1,5-a][1,3,5]-triazine (1.40 g) and triethylamine (1.01 g) in 1,2-dimethoxy ethane (100 ml) and methanol (50 ml), and the stirring was continued overnight. The solvent was then evaporated and the residue was purified by chromatography on silica-gel eluting with dichloromethane containing methanol 10% v/v and ammonia 1% v/v. The residue obtained (1.8 g) was then treated with activated charcoal, and was then converted in methanol solution to the hydrochloride salt. The hydrochloride salt was purified further by chromatography on silica-gel eluting with dichloromethane containing methanol 5% v/v and ammonia 1%, to afford 7-amino-2-(2-furyl)-5-[2-[(4-dimethylaminoethyl-N-methylsulphonamido)phenyl]ethyl]amino[1,2,4]-triazolo[1,5-a][1,3,5]-triazine (0.58 g); microanalysis found C, 51.1; H, 5.6, N, 25.1; $H_2O$, 2.2%; $C_{21}H_{27}N_9O_3S$ 0.5 $H_2O$ requires C, 50.9; H, 5.65; N, 25.4; $H_2O$, 1.8% NMR: 2.70 (s, 3H, N-CH3), 2.95 (s, 6H, N(CH3)2), 3.04 (complex, 2H, CH2Ar), 3.30(sbr, 4H, CH2-N), 3.68(complex, 2H, CH2N), 6.65(d of d, 1H, furyl-4H), 7.16(d, 1H, furyl-3H) 7.55 and 7.76 ($A_2B_2$ pattern, 4H, phenyl-4H) and 7.78 (s, 1H, furyl-5H); m/e 486 $(M+H)^+$.

The necessary starting materials were prepared as follows:

(1) To a solution of 4-(N-2-acetylaminoethyl)benzenesulphonyl chloride (5.23 g) [see E. H. Schweizer et al. J. Med. Chem., 1983, 26, 964–970) in dichloromethane (75 ml) was added N,N,N'-trimethyl-1,2-ethylene diamine (2.04 g) and the mixture was stirred at ambient temperature overnight. The solvent was then removed by evaporation and the residue was purified by chromatography on silica-gel, eluting with dichloromethane containing methanol 10% v/v and ammonia 880 1% v/v. Evaporation of the solvent from the appropriate fractions gave 4-(N-2-acetylaminoethyl)-N,N,N'-(trimethylamino)ethylbenzene sulphonamide; NMR: 1.95 (s, 3H, NHCOCH3), 2.24(s, 6H, N(CH3)2), 2.48(t, 2H, CH2Ar), 2.79 (s, 3H, NCH3), 2.90 (t, 2H, CH2N), 3.12 (t, 2H, CH2N), 3.51(q, 2H, NHCH2), 5.60 (brs, 1H, NHCOCH3) and 7.34 and 7.73 ($A_2B_2$ pattern, 4H, phenyl H); m/e 328 $(H+H)^+$.

(2) A mixture of 4-(N-2-acetylaminoethyl)-N,N,N'-trimethylamino)ethylbenzene sulphonamide (3.4 g) and 2M hydrochloric acid (75 ml) were heated on a steam bath overnight. The solvent was then removed by evaporation and the residue was dissolved in ethanol, the solution filtered and the solvent removed by evaporation to give (4-Dimethylaminoethyl-N-methylsulphonamido)phenylethylamine hydrochloride as a white solid; m.p. 225°–9° C.; NMR: 2.76(s, 3H, N-CH3), 2.92 (s, 6H, N(CH3)2), 3.15 (complex, 4H, NCH2CH2CH2Ar) and 3.37 (s, 4H, NCH2CH2N) and 7.56 and 7.77 ($A_2B_2$ pattern, 4H, phenyl-H); m/e 286 $(M+H)^+$.

(3) Hydrogen chloride gas (20.0 g) was bubbled into an ice-cooled mixture of 2-furonitrile (46.5 g) and absolute ethanol (23.0 g). After addition of the gas, solid crystallised from the mixture. The crystalline solid was collected by filtration and heated in pyridine (300 ml) with aminoguanidine nitrate (56.0 g) under reflux for 4 hours. The mixture was cooled, solid material removed by filtration and the filtrate evaporated to give crude 3-amino-5-(2-furyl)-1,2,4-triazole. This material was purified by treatment with nitric acid (400 ml of 50% v/v). The crystalline salt which formed was collected by filtration, washed sequentially with water (100 ml) and ethanol (50 ml) and air dried to give 3-amino-5-(2-furyl)-1,2,4-triazole nitrate (45.0 g), m.p. 130°–133° C. (decomp.). Several batches (184.0 g) of this salt (184 g) were suspended in hot water (400 ml) and sodium carbonate (46.0 g) was added in portions. The basic solution obtained was allowed to cool to give 3-amino-5-(2-furyl)-1,2,4-triazole (82.0 g) as colourless prisms, m.p. 204°–206° C.; NMR 6.05(s, 2H, NH2), 6.6(s, 1H, furyl-4H), 6.7(s, 1H, furyl-3H), 7.7(s, 1H, furyl-5H), 12.05(br s, 1H NH).

(4) An intimate mixture of 3-amino-5-(2-furyl)-1,2,4-triazole (33.0 g) and dimethyl N-cyanodithioiminocarbonate (33.0 g) was heated at 170° C. for 1 hour, under a slow stream of argon. After cooling, the resulting solid was purified by column chromatography on silica (600 g) eluting with an increasing amount of ethyl acetate in dichloromethane (5–10% v/v) to give 7-amino-2-(2-furyl)-5-methylthio-[1,2,4]triazolo[1,5-a][1,3,5]triazine as a colourless solid (11.1 g), essentially pure by TLC, which was used without further purification. [A small amount of the above solid was recrystallised from ethanol and gave, crystals, m.p. 238°–240° C.; microanalysis, found: C, 44.0; H, 3.3; N, 33.7; $C_9H_8N_6SO/0.05C_2H_5OH$ requires C, 43.6; H, 3.3; N, 33.6; NMR 1.05 and 3.4 (t+q, ethanol of crystallisation), 2.5 (s, 3H, CH3S—), 6.7(dd, 1H, furyl-4H), 7.2(d, 1H, furyl-3H), 7.7(d, 1H, furyl-5H) 8.7–9.0(br d, 2H, NH2); m/e 248 $(M^+)$.

(5) A solution of 3-chloroperoxybenzoic acid (50% strength, 45.0 g) in dichloromethane (300 ml) was added to a stirred, ice-cooled suspension of 7-amino-2-(2-furyl)-5-methylthio-[1,2,4]triazolo-[1,5-a][1,3,5]triazine (8.0 g) in dichloromethane (300 ml). The residual aqueous layer was discarded. The resulting suspension was allowed to warm to ambient temperature and stirred for 16 hours. The solvent was evaporated and ethanol (150 ml) was added to the residue. The suspension obtained was left to stand for 30 minutes with occasional swirling. The solid was then collected by fitration, washed with ethanol and dried to give 7-amino-2-(2-furyl)-5-methylsulphonyl-[1,2,4]triazolo[1,5-a][1,3,5]triazine (6.6 g) as a colourless solid, NMR: 3.3(s, 3H, $CH_3.SO_2$), 6.7(q, 1H, furyl-4H), 7.3(q, 1H, furyl-3M), 7.9(q, 1H, furyl-5H), 9.4–9.8(d, 2H, $NH_2$), which was used without further purification.

EXAMPLE 2

7-Amino-2-(2-furyl)-5-[2-[(4-dimethylaminopropyl-N-methyl-sulphonamido)phenyethyl]amino[1,2,4]-triazolo[1,5-a1,3,5]-triazine (4-Dimethylaminopropyl-N-methylsulphonamido)-phenyhthylamine hydrochloride (3.3 g) was added to a stirred suspension of 7-amino-2-(2-furyl)-5-methylsulphonyl-[1,2,4]triazolo[1,5-a][1,3,5]triazine (1.4 g) and triethylamine (1.01 g) in 1,2-dimethoxyethane (100 ml), methanol (50 ml) and the stirring was continued overnight. The solvent was evaporated and the residue was purified by chromatography on silica-gel, eluting with dichloromethane containing methanol 10% v/v and ammonia (1% v/v). The product (1.9 g) obtained was crystallised from ethanol and gave a solid (1.8 g). A part of this solid (0.8 g) was dissolved in methanol and the solution acidified with ethereal hydrogen chloride. The methanol was then evaporated and the residue crystallised from ethanol:ethyl acetate to afford 7-amino-2-(2-furyl)-5-[2-[(4-dimethylaminopropyl-N-methylsulphonamido)phenyl]ethyl]amino[1,2,4]-triazolo[1,5-a][1,3,5]triazine as an amorphous solid; micro analysis, found: C, 45.9; H, 5.7; N, 21.6%; $C_{22}H_{29}N_9O_3S.2HCl$ requires C 46.2; H, 5.5; N, 22.0%; NHR: 1.90(complex, $CH_2$), 2.67(s, 3H, $N-CH_3$), 2.79(s, 6H, $N(CH_3)_2$), 3.04(complex, 6H, ($N-CH_2CH_2N$) and $CH_2Ar$) 3.64(complex, 2H, $NCH_2$), 6.73(S, 1H, furyl-4H), 7.27(d, 1H, furyl-3H) 7.53 and 7.72($A_2B_2$ pattern, 4H, phenyl-H) and 7.92 (s, 1H, furyl-5H); m/e 500 $(M+H)^+$.

The necessary starting material was prepared as follows:

(1) In a manner similar to that described in Example 1, part (1), but starting from 4-(N-2-acetylaminoethyl)-benzenesulphonyl chloride and N,N,N'-trimethyl-1,3-propane diamine there was obtained 4-(N-acetylaminoethyl)-N,N,N'-trimethylamino)propylbenzenesulphonamide; NMR: 1.7 (quartet, 2H, $CH_2$) 1.94 (s, 3H, $NHCOCH_3$), 2.20 (s, 6H, $N(CH_3)_2$), 2.31 (t, 2H, $CH_2Ar$), 2.74 (s, H, $NCH_3$), 2.89 (t, 2H, $CH_2N$), 3.05 (t, 2H, $CH_2N$), 3.47 (q, 2H, $CH_2NH$), 5.76 (br s, 1H, $NHCOCH_3$) and 7.34 and 7.70 ($A_2B_2$ pattern, 4H, phenyl-4H); m/e 342 $(H+H)^+$.

(2) In a similar manner to that described in Example 1, part (2) there was obtained (4-dimethylaminopropyl-N-methylsulphonamido)phenylethylamine hydrochloride; m.p. 195°–9° C.; NMR: 1.91 (complex, 2H, $CH_2$), 2.68 (s, 3H, N $CH_3$), 2.72 (s, 6H, $N(CH_3)_2$), 3.02 (s, 8H, $CH_2N$ and $CH_2Ar$) and 7.53 and 7.73 ($A_2B_2$ pattern, 4H, phenyl-H); m/e 300 $(M+H)^+$.

EXAMPLE 3

7-Amino-2-(2-furyl)-5-[2-[(4-dimethylaminobutyl sulphonamido)phenyl]ethyl]amino[1,2,4]-triazolo[1,5-a][1,3,5]triazine (4-Dimethylaminobutylsulphonamido)phenylethylamine hydrochloride (4.3 g) was added to a stirred suspension of 7-amino-2-(2-furyl)-5-methylsulphonyl-[1,2,4]triazolo[1,5-a][1,3,5]-triazine (1.40 g) and triethylamine (1.01 g) in 1,2-dimethoxyethane (100 ml) and methanol (50 ml), and the stirring was continued overnight. The solvent was then evaporated and the residue was purified by chromatography on silica-gel, eluting with dichloromethane containing methanol 12% v/v and ammonia 1% v/v. The residue obtained (2.5 g) was crystallised from ethanol to give a solid (2.3 g). A part of this solid (1.1 g) was dissolved in methanol (10 ml) and the solution was acidified with ethereal hydrogen chloride. The solvent was then evaporated. The residue was then dissolved in ethanol and treated with charcoal. The solvent was then evaporated and the residue treated with hot ethyl acetate to afford 7-amino-2-(2-furyl)-5-[2-[(4-dimethylaminobutylsulphonamido)-phenyl]ethyl]amino[1,2,4]-triazolo[1,5-a][1,3,5]triazine as an amorphous solid; microanalysis, found: C, 47.2; H, 5.9; N, 20.6%; $C_{22}H_{29}N_9O_3S$ 2HCl 0.3 $CH_3CO_2Et$ requires C, 46.8; H, 5.7; N, 21.0%; NMR: 1.45 (complex, 2H, $CH_2$), 1.67 (complex, 2H, $CH_2$), 2.73 (complex 8H, $CH_2Ar$ and $N(CH_{32})$, 3.0 (t, 2H, $CH_2N$), 3.62(br, 2H, $NCH_2$), 6.71(s, 1H, furyl-4H), 7.24 (d, 1H, furyl-3H), 7.49 and 7.76 ($A_2B_2$ pattern, 4H, phenyl-H) and 7.91 (s, 1H, furyl-5H); m/e 500 $(M+H)^+$.

The necessary starting material was prepared as follows:

In a manner similar to that described in Example 1, part (1), but starting from 4-(N-2-acetylaminoethyl)benzenesulphonyl chloride and 4-(N,N-dimethylamino)-butylamine there was obtained 4-(N-acetylaminoethyl)-N,N-dimethylamino)butanebenzene sulphonamide; NMR: 1.53(complex, 4H, $CH_2$), 1.93 (s, 3H, $NHCOCH_3$), 2.23 (complex, 8H, $CH_2Ar$ and $N(CH_3)_2$), 2.88 (complex, 4H, $CH_2N$), 3.48 (q, 2H, $CH_2NH$), 5.91 (t, 1H, $NHCOCH_3$) and 7.31 and 7.75 ($A_2B_2$ pattern, 4H, phenyl-4H) m/e 342 $(M+H)^+$.

(2) In a manner similar to that described in Example 1, part (2) there was obtained also 4-dimethylaminobutylsulphonamido)phenylethylamine hydrochloride m.p. 176°–80° C.; NMR: 1.51 (complex, 2H, $CH_2$), 1.68 (complex, 2H, $CH_2$), 2.79 (s, 6H, $N(CH_3)_2$, 2.82 (complex, 2H, $CH_2Ar$), 3.07 (complex, 4H, $CH_2N$), 3.17 (complex, 2H, $CH_2N$) and 7.49 and 7.81 ($A_2B_2$ pattern, 4H, phenyl-H); m/e 300 $(M+H)^+$.

EXAMPLE 4

The following illustrate representative pharmaceutical dosage forms containing a compound of formula I, for example as illustrated in any of the previous Examples, (hereafter referred to as "compound X"), for therapeutic or prophylactic use in humans:

| (a) Tablet | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

-continued

| (b) Capsule | mg/capsule |
|---|---|
| Compound X | 10 |
| Lactose Ph.Eur | 488.5 |
| Magnesium stearate | 1.5 |

The above formulations may be obtained by conventional procedures well known in the pharmaceutical art. The tablets may be enteric coated by conventional means, for example to provide a coating of cellulose acetate phthalate.

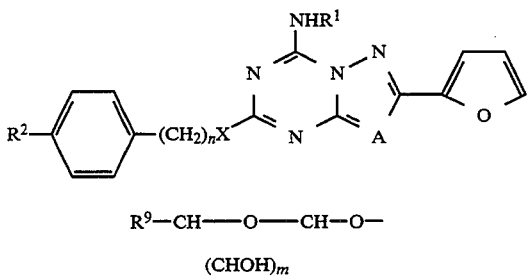

I

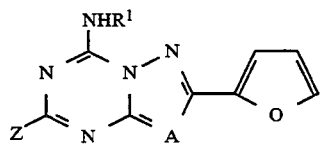

II (CHOH)$_m$

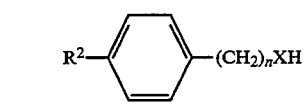

III

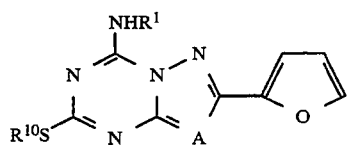

IV

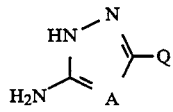

V

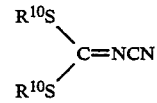

VI

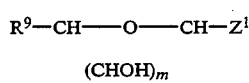

VII

R$^9$—CH——O——CH—Z$^1$

IX (CHOH)$_m$

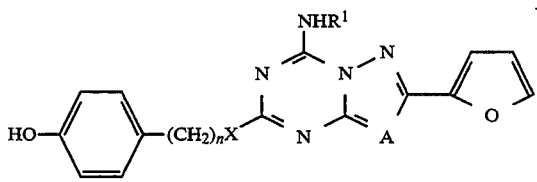

VIII

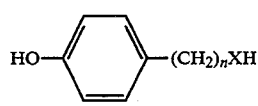

X

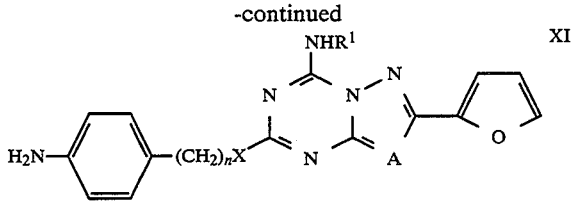

XI

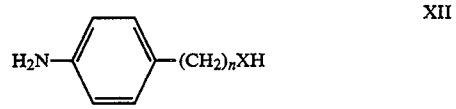

XII

What is claimed is:
1. A compound of the formula I

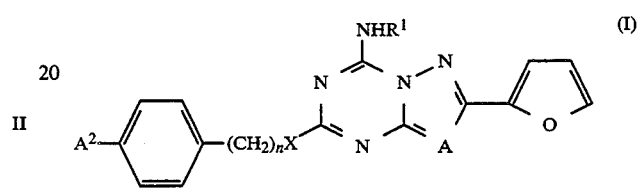

(I)

wherein:
X is O, S or NH;
n is 0 or an integer of from 1 to 3;
R$^1$ is hydrogen, (1–6C)alkyl, or (1–4C)alkanoyl;
R$^2$ is CH$_2$R$^3$, NHR$^4$, SO$_2$NR$^5$YNR$^6$R$^7$ or R$^8$, in which R$^3$ is hydroxy, (1–4C) alkoxy or (1–4C) alkylsulphonyl; R$^4$ is (1–4C) alkylsulphonyl, (1–4C) haloalkylsulphonyl, formyl, carbamoyl or 2,6-dichloro-4-(2-(1,1-dimethylethyl)amino-1-hydroxyethyl)phenyl;
R$^5$ is hydrogen or (1–4C) alkyl; Y is CO or (1–6C) alkylene; R$^6$ and
R$^7$ are independently (1–4C)alkyl, or R$^6$ is hydrogen and R$^7$ is (1–4C) alkyl, (1–4C) haloalkyl, phenyl (1–4C) alkyl or, when Y is (1–6C) alkylene, is (1–4C) alkylaminocarbonyl or (5–6C)cycloalkylaminocarbonyl; and R$^8$ is a sugar residue of formula II

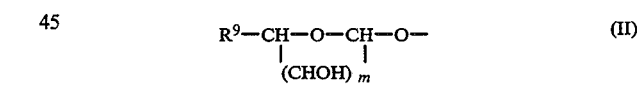 (II)

in which R$^9$ represents hydrogen, methyl or hydroxymethyl and m is 2 or 3;
A is N or CT in which T is hydrogen or (1–4C)alkyl; or a pharmaceutically acceptable salt thereof.
2. A compound as claimed in claim 1, in which R$^2$ is CH$_2$R$^3$, NHR$^4$, SO$_2$NR$^5$YNR$^6$R$^7$ or R$^8$, in which R$^3$ is hydroxy, methoxy, ethoxy, methylsulphonyl or ethylsulphonyl; R$^4$ is methylsulphonyl, ethylsulphonyl, butylsulphonyl, trifluoromethylsulphonyl, formyl, carbamoyl or 2,6-dichloro-4-(2-( 1,1-dimethylethyl)amino-1-hydroxyethyl)phenyl; R$^5$ is hydrogen, methyl or ethyl; Y is CO, ethylene, propylene or butylene; R$^6$ and R$^7$ and are independently methyl or ethyl, or R$^6$ is hydrogen and R$^7$ is methyl, ethyl, trifluoromethyl, benzyl, or, when Y is ethylene, propylene or butylene, is methylaminocarbonyl or cyclopentylaminocarbonyl; and R$^8$ is L-arabinofuranosyl, D-xylofuranosyl, 6-deoxy-D-galactopyranosyl, 6-deoxy-L-galactopyranosyl, D-galactopyranosyl, D-glucopyranosyl or D-mannopyranosyl.

3. A compound as claimed in claim 1, in which $R^2$ is $SO_2NR^5YNR^6R^7$, in which $R^5$ is hydrogen, methyl or ethyl; Y is CO, ethylene propylene or butylene; $R^6$ and $R^7$ are independently methyl or ethyl, or $R^6$ is hydrogen and $R^7$ is methyl, ethyl, trifluoromethyl, benzyl, or, when Y is ethylene, propylene or butylene, is methylaminocarbonyl or cyclopentylaminocarbonyl.

4. A compound as claimed in claim 3, in which Y is ethylene, propylene or butylene, and $R^6$ and $R^7$ are both methyl.

5. A compound as claimed in claim 1 or claim 2, in which $R^1$ is hydrogen and A is N.

6. A compound as claimed in claim 1 or claim 2, in which n is 2.

7. A compound as claimed in claim 1 or claim 2, in which X is NH.

8. A compound selected from:
7-amino-2-(2-furyl)-5-[2-[(4-dimethylaminoethyl-N-methylsulphonamido)phenyl]ethyl]amino[1,2,4]-triazolo[1,5-a][1,3,5]triazine, 7-amino-2-(2-furyl)-5-[2-[(4-dimethylaminopropyl-N-methylsulphonamido)phenyl]ethyl]amino[1,2,4]triazolo[1,5-a][1,3,5]triazine, and 7-amino-2-(2-furyl)-5-[2-[(4-dimethylaminobutylsulphonamido)phenyl]ethyl]amino[1,2,4]triazolo[1,5-a][1,3,5]triazine.

9. A method of antagonising one or more of the vasodilatory actions of adenosine in a warm-blooded animal requiring such treatment by administering an effective amount of a compound of formula I as defined in claim 1, or a pharmaceutically acceptable salt thereof.

10. A pharmaceutical composition, which comprises a compound of formula I as claimed in claim 1, or a pharmaceutically acceptable salt thereof, in admixture or together with a pharmaceutically acceptable diluent or carrier.

* * * * *